United States Patent [19]

Baillie et al.

[11] Patent Number: 4,776,210
[45] Date of Patent: Oct. 11, 1988

[54] MULTIPHASE FLUID FLOW MEASUREMENT SYSTEMS AND METHODS

[75] Inventors: Lloyd A. Baillie; Frank H. Hsu; Y. Sam Yang, all of Plano, Tex.

[73] Assignee: Atlantic Richfield Company, Los Angeles, Calif.

[21] Appl. No.: 57,549

[22] Filed: Jun. 3, 1987

[51] Int. Cl.$^4$ ............................................. G01N 33/28
[52] U.S. Cl. ................................. 73/61.1 R; 73/861.04
[58] Field of Search ............. 73/61.1 R, 861.04, 61 R, 73/32 R

[56] References Cited

U.S. PATENT DOCUMENTS

| | | | |
|---|---|---|---|
| 4,144,754 | 3/1979 | Pitts, Jr. et al. | 73/861.04 |
| 4,215,567 | 8/1980 | Vleck | 73/61.1 R |
| 4,429,581 | 2/1984 | Furmaga | 73/861.04 |
| 4,596,136 | 6/1986 | Zacharias | 73/61.1 R |
| 4,656,869 | 4/1987 | Zacharias | 73/61.1 R |
| 4,660,414 | 4/1987 | Hatton et al. | 73/61.1 R |
| 4,689,989 | 9/1987 | Asiesen et al. | 73/61.1 R |

*Primary Examiner*—Michael J. Tokar
*Assistant Examiner*—Hezron E. Williams
*Attorney, Agent, or Firm*—Michael E. Martin

[57] ABSTRACT

The total mass flowrate of a multiphase fluid flowstream such as a water, oil and gas mixture being produced from subterranean wells is determined by passing the flowstream through an apparatus which forces a substantial change in direction of the fluid flowstream and wherein a pressure differential is measured across flow paths of known cross-sectional flow area. The total mass flow is determined from the cross-sectional flow areas, the measured total density of the flowstream and the differential pressure. A sample of the flowstream is withdrawn from the flow path, gas is separated from liquid and the liquid fraction of water is measured by passing the liquid mixture through a device which measures the dielectric constant of the liquid mixture using microwave radiation transmissivity or differential pressure between columns of the liquid mixture and a column of water of equal height is compared. Total density of the flowstream may be obtained by measuring differential pressures across changes in elevation of the flowstream.

17 Claims, 3 Drawing Sheets

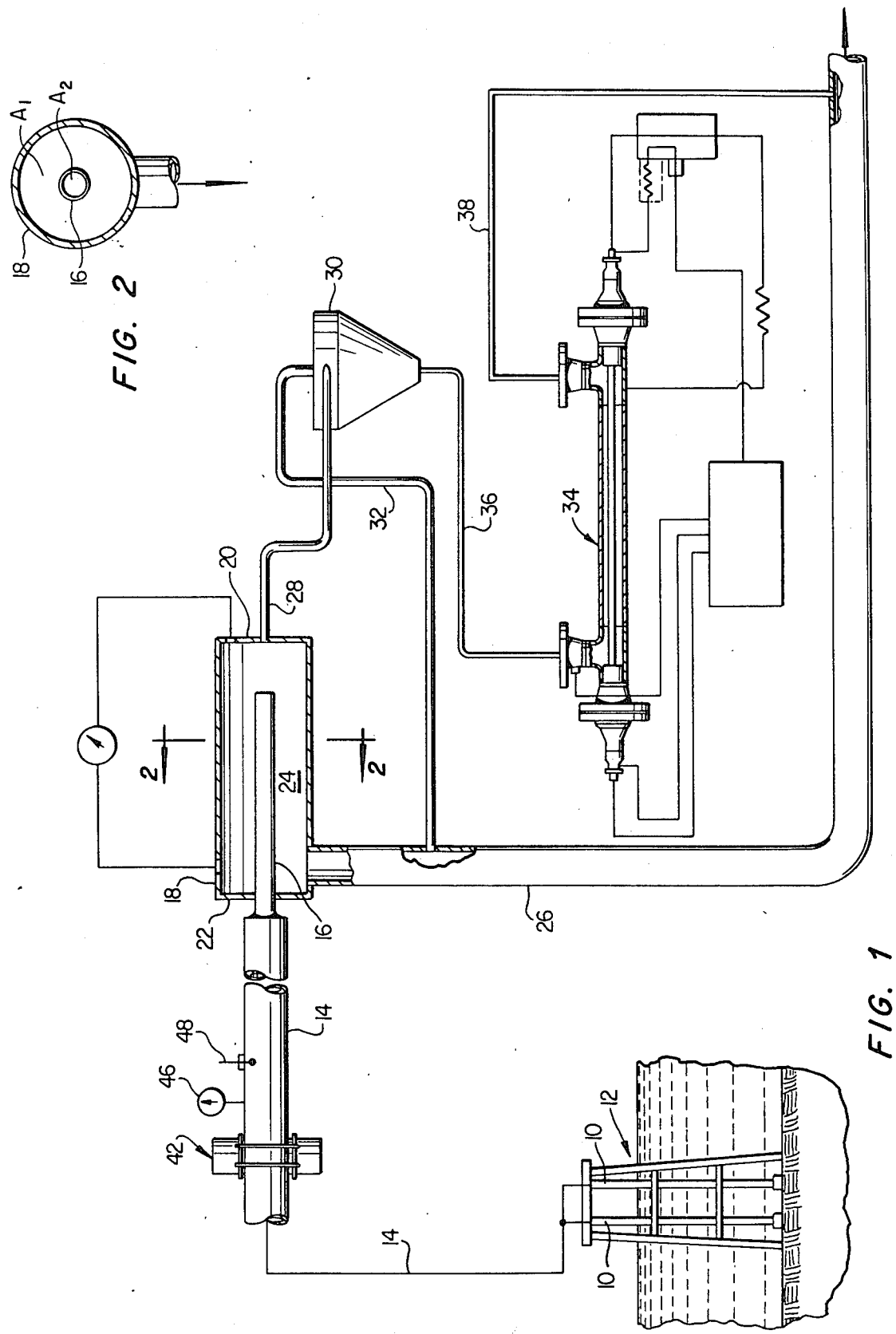

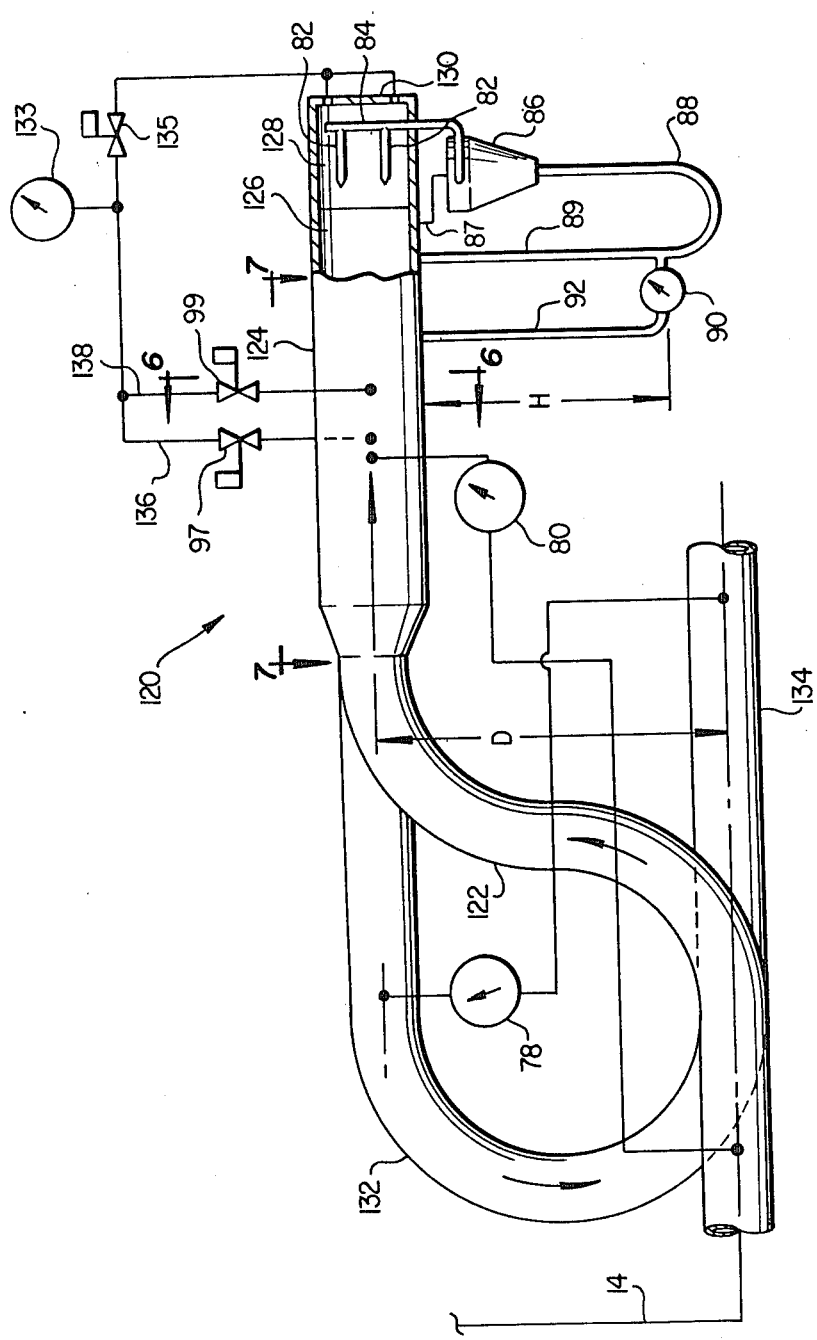
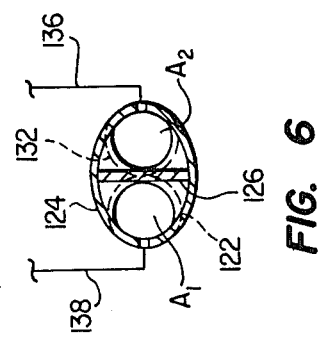
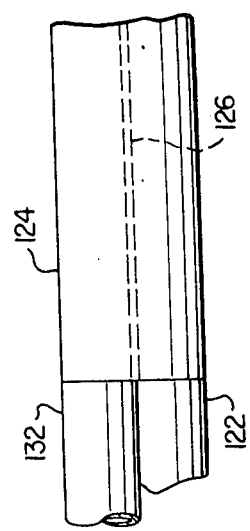
FIG. 6
FIG. 7
FIG. 5

MULTIPHASE FLUID FLOW MEASUREMENT SYSTEMS AND METHODS

BACKGROUND OF THE INVENTION

1. Field of the Invention

The present invention pertains to systems for measuring multiphase fluid flow, particularly mixtures of oil, water and gas, by determining the density of the multiphase mixture, the mass flow rate by change of momentum and the proportion of water and oil by measuring the dielectric properties of a separated flow stream of liquid, or by measuring the pressure differential of identical height columns of a water-oil mixture and water alone, respectively.

2. Background

In the production of hydrocarbon fluids from subterranean wells, it is common to be required to handle a multiphase fluid mixture comprising primarily crude oil, water and gas. For various reasons it is important to be able to determine the mass flow rate of each component of such a mixture from each well or from a selected number of wells which deliver their production into a common manifold or flowline.

Conventional apparatus for measuring the flow of fluids produced from oil wells requires separation of the components and measurements by conventional single phase fluid measuring devices. This type of equipment takes up a considerable amount of space, is expensive and is not usually suitable for continuously monitoring the fluid produced from a well or a selected number of wells. Accordingly, it has been considered highly desirable to provide a multiphase mass flow meter that does not require substantial separation processes, is compact enough to be considered for installation on offshore production platforms and the like, and can essentially be interposed in the main fluid flowline through which the produced fluids are conducted. Since it would be desirable also to provide such a mass flow measuring system on each well flowline or a well flowline from a selected number of wells, the cost of such a system must also be given serious consideration.

SUMMARY OF THE INVENTION

The present invention provides an improved method and system for measuring multiphase fluid flowstreams to determine the flowrate of the various components of the flowstream wherein the total mass flowrate may be determined by measuring the density of the multiphase fluid flowstream and by measuring a pressure change in the flowstream as it flows through a path of known cross-sectional area.

In accordance with one important aspect of the present invention, the total mass flowrate of a multiphase fluid flowstream is measured by the change in momentum of the flowstream which is determined by causing a flow reversal of the stream in a duct apparatus having a change in cross-sectional flow area and wherein the pressure differential caused by the change in momentum and the cross-sectional flow area of the passage is used to determine the mass flowrate. In one embodiment of the invention, the total fluid flowstream density is measured directly by a densitometer such as a gamma ray type density measuring device and in an alternate embodiment of the invention, the density of the flow stream is measured by measuring the pressure differential between two elevations of the flowstream. In accordance with another aspect of the present invention, the ratio of liquid flow to gas flow is determined by withdrawing a sample of the flowstream from its main flowpath, performing a gas/liquid separation procedure and measuring the ratio of the components of the liquid mixture by a selected procedure, including but not limitd to measurement of microwave radiation transmissivity or difference in pressure of two columns of liquid wherein one of the liquid columns is a known component of the liquid mixture.

The present invention provides improved methods and systems particularly adapted for measuring the total flow of a gas, water and oil mixture in flowstreams of produced well fluids and the like. The apparatus minimizes the space required for flow measuring equipment, is mechanically uncomplicated and does not interrupt the flowstream by requiring separation of the fluid into components upstream of primary separating equipment. In this regard, the systems of the present invention are particularly adapted for installation on or in proximity to crude oil producing facilities, such as offshore production platforms wherein the main flowstream of the produced fluids may then be comingled with additional flowstreams and pumped to onshore or remotely located separation facilities.

Those skilled in the art will recognize the abovedescribed features and advantages of the present invention, together with other superior aspects thereof upon reading the detailed description which follows in conjunction with the drawing.

BRIEF DESCRIPTION OF THE DRAWING

FIG. 1 is a somewhat schematic illustration of a preferred embodiment of a system for measuring the flow rate of a gas/liquid mixture in accordance with the present invention;

FIG. 2 is a section view taken generally along the line 2—2 of FIG. 1;

FIG. 5 is a somewhat schematic diagram of a second alternate embodiment of a system in accordance with the present invention;

FIG. 6 is a section view taken along the line 6—6 of FIG. 5; and

FIG. 7 is a detail view taken from the line 7—7 of FIG. 5.

DESCRIPTION OF THE PREFERRED EMBODIMENTS

Figures 3, 4:
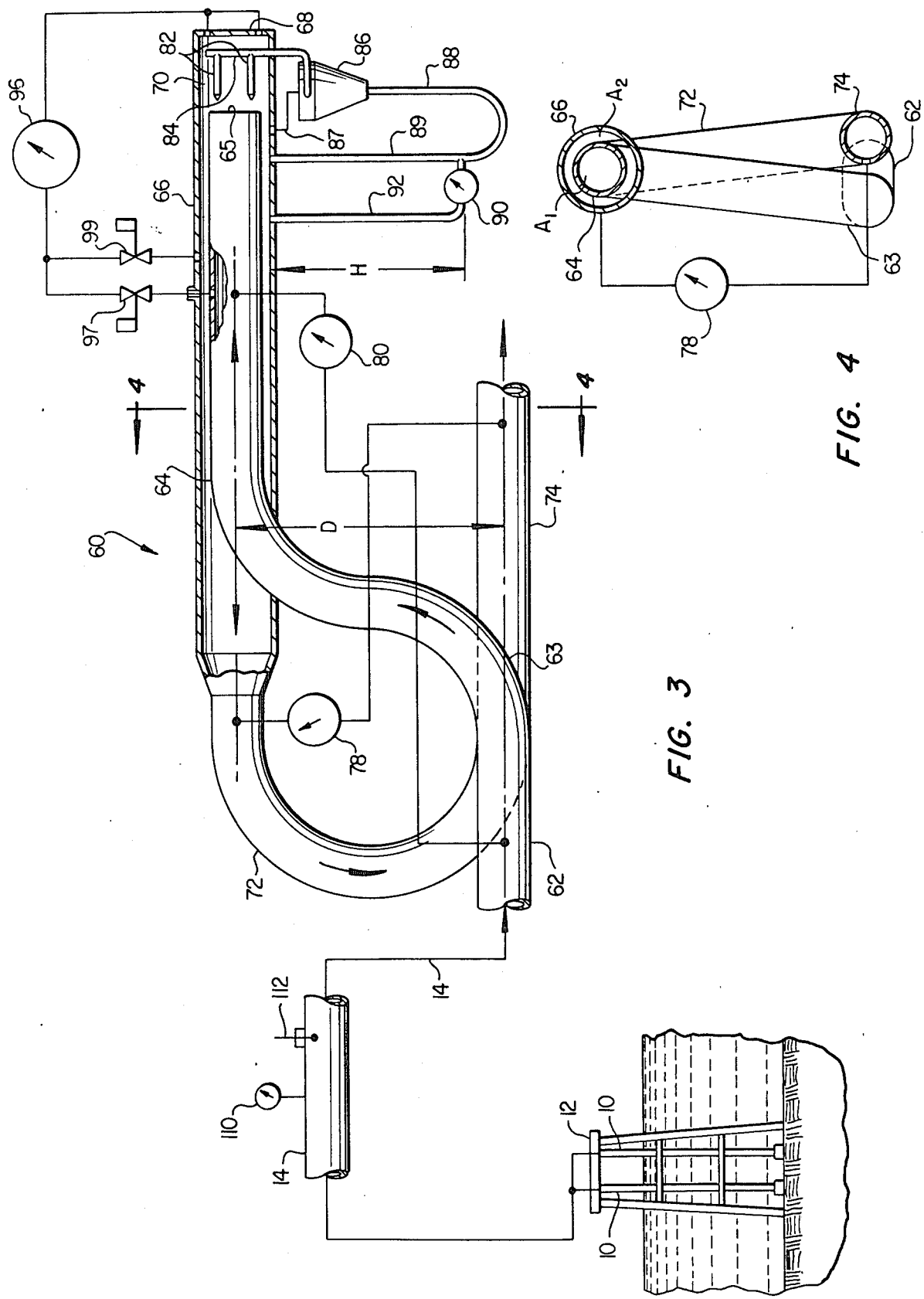
FIG. 3 is a somewhat schematic diagram of an alternate embodiment of a system in accordance with the present invention.
FIG. 4 is a section view taken along the line 4—4 of FIG. 3.

In the description which follows like components are marked with the same reference numerals, respectively. The drawing figures are not inteneed to be to scale and certain features of the invention are shown in schematic form in the interest of clarity and conciseness. Conventional elements may be identified by simplified symbols.

Referring to FIG. 1, there is illustrated a source of multiphase fluid comprising primarily natural gas, water and crude oil which is being produced from a subterranean formation through production risers 10 connected to an offshore production platform 12. The production risers 10 are operably associated with wells which are producing the multiphase fluids. Due to the various arrangements of production flowline networks which may be interconnected in an offshore as well as an onshore oil field, it is desirable to know the flow rate of the components of a multiphase fluid flowstream from each well or a closely associated group of wells for economic and regulatory reasons. It is also desirable in many instances that complicated separation equipment, which the flowstreams must eventually be passed through, be located at a single site for separating the combined flowstreams of many wells. In connection with offshore production systems, it is desirable that such separation equipment be located on a common platform or possibly onshore. Moreover, in order to minimize the pumping costs for delivering the fluids produced from the risers 10, it is also desirable that the flow measuring equipment minimize the flow losses encountered by the production flowstream.

The apparatus illustrated in FIG. 1 may be disposed on the platform 12 and includes a production fluid conduit 14 suitably connected to the risers 10. The conduit 14 includes a reduced diameter nozzle section 16 extending into an enlarged diameter portion of the conduit comprising an elongated cylindrical conduit section 18. The conduit section 18 includes a transverse end wall 20 and an end wall 22 at the opposite end defining in part an interior chamber 24. A flow exit conduit 26 having essentially the same diameter as the conduit 14 opens into the chamber 24 near the end wall 22. The conduit 26 leads to further facilities for handling the flowstream of water, oil and gas, not shown. A fluid sample withdrawal conduit 28 preferably opens into the chamber 24 directly in line with the nozzle section 16 for receiving a continuous sample of the fluid flow entering the chamber 24 and impacting against the end wall 20. The conduit 28 is connected to a centrifugal separator 30 or a similar type separator for separating gas and liquid. The gas phase of the multiphase fluid flowstream entering the separator 30 is withdrawn through a conduit 32 and reinjected into the flowstream by way of the conduit 26 as illustrated.

The liquid separated from the gas phase is conducted to an apparatus 34 of a type which measures microwave eletromagnetic radiation transmissivity through the combined water-oil liquid mixture for measurement of the water fraction of the liquid mixture. The apparatus 34 is preferably of a type described in U.S. patent application Ser. No. 06/932,068 filed Nov. 18, 1986, in the name of Bentley N. Scott and Y. Sam Yang and assigned to the assignee of the present invention. Similar devices of less accuracy and lacking the unique features of the apparatus 34 and of a known type may be substituted for the apparatus 34 for determining the water and oil fraction of the liquid mixture. The sample liquid mixture is conducted to the apparatus 34 by way of a conduit 36 connected to the separator 30 and the sample liquid mixture is then returned to the conduit 26 through a conduit 38.

Referring to FIG. 2, it will be noted that the total cross-sectional area of the interior of the chamber 24 may be determined from the annular cross-sectional area defined between the outside diameter of the nozzle 16 and the inside diameter of the cylindrical conduit section 18. The annular cross-sectional area is designated by the numeral $A_1$. The cross-sectional area of the nozzle 16 is designated by the symbol $A_2$ and, ignoring the wall thickness of the nozzle 16, the total cross-sectional area is $$A = A_1 + A_2. \quad (1)$$

The basic principles under which the systems of the present invention operate are based on the measurement of three parameters, namely the density of the fluid mixture, the total mass flowrate of the fluid mixture and the fractional component of the water and oil of the liquid portion of the mixture. Three equations that describe the total measurement system are as follows:

$$m_t = m_o + m_w + m_g \quad (2)$$

$$\rho_t = \rho_L(1-n) + \rho_g n \quad (3)$$

$$\rho_L = \rho_o(1-b) + \rho_w b \quad (4)$$

wherein m refers to mass flowrate, $\rho$ is density, n is the fraction of the total volume which is gas and b is the fraction of the liquid volume which is water. The subscripts t, o, w and g refer to the total composition and the oil, water and gas compositions or components, respectively. The subscript L refers to liquid.

From the foregoing equations, it may also be proposed hhat the fraction of the total volume flowrate ($Q_t$) which is gas and the fraction of liquid volume ($Q_L$) which is water are as follows:

$$n = \frac{Q_g}{Q_t} \quad (5)$$

$$b = Q_w/Q_L \quad (6)$$

Still further, the mass flow rates of the respective components of the mixture may be determined from the following equations:

$$m_o = \frac{\rho_o}{\rho_t}(1-n)(1-b)m_t \quad (7)$$

$$m_w = \frac{\rho_w}{\rho_t}(1-n)b \, m_t \quad (8)$$

$$m_g = \frac{\rho_g}{\rho_t} n \, m_t \quad (9)$$

In accordance with the embodiment illustrated in FIG. 1, the total density of the flowstream being conducted through the conduit 14 may be determined by a densitometer, generally designated by the numeral 42. The densitometer may be of a type commercially available and based on the principle of attenuation of gamma rays. One source of a densitometer of a type which is operable with the present invention is manufactured by Texas Nuclear of Austin, Tex. as their Type SGD Digital Density Gauge. This type of apparatus is not required to be interposed in the conduit 14 but is merely a strap-on type device which may be secured to the exterior of the conduit.

The apparatus illustrated in FIGS. 1 and 2 is adapted to measure the total mass flowrate of the multiphase fluid flowstream by a change of momentum principle. For example, the force F acting on the fluid may be determined from the equation:

$$F = \frac{m_t \Delta V}{g_c} \quad (10)$$

wherein $m_t$ is the total mass flow rate, $\Delta V$ is the change in velocity of the flowstream and $g_c$ is the gravitational and dimensional constant. The mass flowrate in the annular portion of the chamber formed within the conduit section 18 can be balanced with the mass flowrate of the flow through the nozzle portion 16 according to the following equations:

$$\rho_t V_1 A_1 = \rho_t V_2 A_2 \quad (11)$$

$$V_2 = (A_1/A_2) V_1 \quad (12)$$

and since the total mass flow rate $$m_t = A_1 V_1 \rho_t \quad (13)$$

and the force F may be derived from equation (9) then by substitution the total mass flow rate may be derived from the following equation:

$$m_t = \sqrt{A_1 A_2 g_c} \cdot \sqrt{\rho_t \Delta P} \quad (14)$$

where $\Delta P$ is the pressure differential in the chamber 24 before and after the reversal of flow of the fluid mixture. The pressure differential $\Delta P$ may be determined by the differential pressure uage 50 which measures the static pressure at the wall 20 and downstream in the chamber 24.

Since the total density is measured by the densitometer 42 and the composition of the components of the liquid mixture and the gas are assumed to be known (i.e., the flowstream is assumed to be made up of crude oil of a known density, water and gas of a known composition) the densities of the components of the fluid mixture may be determined from conditions of pressure and temperature at the point of measurement using suitable pressure measurement means 46 and temperature sensing means 48. Moreover, the ratio of volume of water to the total liquid mixture may be determined from the measurements taken by the apparatus 34 so that the quantity b is known. Substituting the value of $\rho_L$ from equation (4) into equation (3), equation (3) may be solved for n (the fraction of the total volume which is gas) and the mass flow rates of oil, water and gas can be calculated using equations (7), (8) and (9). Those skilled in the art will recognize that the mathematical analysis hereinbefore described may be carried out automatically on a suitable digital data processing computer using input data from the densitometer 42, a pressure differential as sensed by a differential measurement gauge 50 and conditions of temperature and pressure as measured by the devices 46 and 48. The parameters of $A_1$ and $A_2$, being known, provide thus for continuous calculation of the total mass flowrate. The ratio of water flow to total liquid flow, for example, otherwise known as b, is also continuously derived from the apparatus 34.

Accordingly, by measurement of the change of momentum of the flowstream of a multiphase fluid of known components, such as water, crude oil and gas of known composition, and by measuring the total density and the fraction of the liquid mixture which is water and oil, the mass flow of the components of the flowstream may be obtained without the separation of the entire flowstream and separate measurement of each component's flowrate. The flowrates of the components of the multiphase fluid flowstream may be continuously monitored without interrupting flow and the system for carrying out the measurements may be interposed in a primary fluid delivery conduit in an arrangement which is compact and mechanically uncomplicated.

Referring now to FIGS. 3 and 4, an alternate embodiment of a flow measurement system and method in accordance with the present invention is illustrated and generally designated by the numeral 60. The system 60 includes a conduit section 62 connected to the conduit 14 and being arranged to undergo a change in vertical elevation over a distance D. Preferably, the conduit section 62 has a relatively smooth curved transition from a section 63 to a section 64 which comprises a nozzle somewhat similar to the nozzle 16 in the embodiment of FIG. 1. The nozzle 64 extends within an elongated cylindrical conduit section 66 having a transverse end wall 68 and defining an interior chamber 70. The conduit section 66 is of larger diameter than the conduit section 64 and discharges into a curved conduit section 72 forming a reverse bend of relatively smooth radius which returns the flowstream to a further conduit section 74 at the same vertical elevation as the conduit section 62. The distance between the central longitudinal axes of the conduit section 66 and the conduit section 74 is preferably the same as the distance between the respective central axes of the conduit sections 62 and 64. Differential pressure gauges 78 and 80 are arranged in respective circuits wherein the differential pressure between the fluid in the conduit section 72 at its elevation and the conduit 74 at its lower elevation is measured concomitantly. The differential pressure between the flow stream in the nozzle section 64 and the conduit section 62 is also measured over the same change in elevation by the pressure differential gauge 80.

The nozzle discharge end 65 is spaced from the end wall 68 and provides space for an array of one or more Pitot tubes 82 which are connected to a manifold conduit 84 leading to a gas/liquid separator 86 similar to the separator 30. Liquid leaves the separator 86 through a U-shaped tube 88 and returns to the conduit section 66 downstream in the direction of flow of fluid from the nozzle discharge end 65. The tube 88 is in communication with a differential pressure gauge 90 which is also connected to vertical fluid column member 92 which opens into the interior of the conduit section 66 at a point so that the pressures measured or sensed by the fluids in the leg 89 of the U-tube 88 and the tube or column conduit 92 are at the same pressure. Separated gas is returned to the conduit section 66 through conduit 87 downstream of the nozzle end 65.

In the operation of the system 60, the multiphase fluid flowstream of water, oil and gas, for example, is continuously throughput from the conduit 14 to the conduit section 62 and is discharged into the chamber 70 wherein the flowstream essentially attains zero velocity and reverses its direction of flow, causing an increase in pressure as measured by a differential pressure gauge 96 which senses the static pressure at the end wall 68 and also selectively in the nozzle 64 at a point upstream of the nozzle end 65 or at a point downstream of the nozzle end. Motor operated valves 97 and 99 are operable to select the pressure differential measurement taken by the gauge 96. The total cross-sectional area of the chamber 70, see FIG. 4, is the sum of the annular area $A_2$ between the conduit section 66 and the nozzle 64, plus the cross-sectional area Al of the nozzle 64, ignoring the wall thickness of the nozzle. The total density of the flowstream being conducted through the system 60 may be determined from the equation:

$$\rho_t = \frac{\Delta P_1 + \Delta P_2}{2D} \quad (15)$$

wherein $\Delta P_1$ and $\Delta P_2$ are the pressure differentials measured by the gauges 78 and 80, respectively, and D is the vertical elevation between the respective pressure taps for the pressure differential gauges 78 and 80.

With the total density known, the total mass flow may be calculated using equation (14). The quantity $\Delta P$ in equation (14) for the system 60 is obtained using the differential pressure gauge 96 and averaging the differential pressure measurements taken between the end wall 68 and the annular flow area between the nozzle 64 and the conduit section 66 and the measurement taken between the end wall 68 and the nozzle 64. This averaging process reduces errors due to friction flow-losses.

In operation, the multiphase fluid flow being conducted through the system 60 is sampled by the Pitot tube 82 and the gas fraction is separated from the liquid fraction and returned to the conduit section 66 by way of a conduit 102. Liquid is collected in the U-tube 88 and returns to the conduit 64 through the leg 89. However, a column of water is maintained in the conduit 92 to the same height as the conduit leg 89 and the difference in pressure between these columns is determined from the pressure differential gauge 90. In this way, the volumetric fraction of oil ($q_o$) in the mixture may be determined from the equation:

$$q_o = \frac{\Delta P_3}{H(\rho_w - \rho_o)} \quad (16)$$

wherein $\Delta P_3$ equals the pressure differential measured by the gauge 90, and H is the height of the column of liquid as indicated in FIG. 3. The densities of oil and water are assumed to be known. Upon determining the fraction of oil in the liquid mixture, the fraction of liquid volume which is water may, of course, be determined.

Accordingly, the mass flow rates of oil, water and gas may thus be determined using equations (2) through (9) in the same manner as for the embodiment of FIG. 1. The embodiment of the system illustrated in FIGS. 3 and 4 may be utilized to determine mass flow rates of the gas and liquid components of a multiphase fluid flowstream by measuring pressure differentials caused by a change in momentum of the fluid flowstream and a change in elevation, the latter being used to determine the density of the flowstream. By sampling a small portion of the total fluid flow and separating gas from liquid in the sample, the fraction of water in oil or oil in water may be determined also solely from a pressure differential xeasurement process if there is a measurable difference in the oil and water densities. Those skilled in the art will recognize that the pressure differential gauges 78, 80, 90 and 96 may be adapted to provide suitable signals to a digital computation system which can be used to continuously monitor the total mass flowrate of the fluid stream being conducted through the conduit system 62, 64, 72, and 74. The mass flowrates of the components of gas and respective liquids may also be determined, when the densities of the respective oil, water and gas fractions are assumed from measurements of pressure and temperature taken by suitable means 110 and 112 corresponding to similar means illustrated in the embodiment of FIGS. 1 and 2.

Referring now to FIGS. 5, 6, and 7, a second alternate embodiment of a flow measurement system and method in accordance with the present invention is illustrated and generally designated by the numeral 120. The system 120 is similar in some respects to the system 60 and is adapted to be connected to the conduit 14 as indicated in FIG. 5 in place of the system 60. The system 120 includes an inlet conduit section 122 which transitions from a cylindrical pipe configuration to a somewhat elliptical partitioned conduit section 124. The conduit section 124 is divided into two flow paths by a central longitudinally extending partition 126. The partition 126 extends to a chamber 128 which is delimited by an end wall 130 of the conduit section 124. The conduit section 124 is also connected to a curved conduit section 132 similar to the conduit section 72 which curves into a lower elevation conduit section 134 for conducting the multiphase fluid flow mixture to a further destination. An advantage of the system 120 is that the cross-sectional flow area of the incoming flow stream, area $A_1$, and the cross-sectional flow area of the outgoing flow stream, area $A_2$, after impingement against the wall 130 are equal. The flow areas $A_1$ and $A_2$ are defined by the conduit section 124 and the respective opposite sides of the partition 126. Moreover, not only are the flow areas $A_1$ and $A_2$ equal, but the surface areas defining the flow paths of the incoming and outflowing flowstreams are also equal so that any frictional pressure losses incurred between the incoming flowstream and the endwall 130 and the outgoing flowstream and the endwall 130 are substantially equal.

As shown in FIG. 5, the endwall 130 is provided with suitable openings for connection to a pressure gauge 133 by way of a motor operated shutoff valve 135. The gauge 133, in turn, is also adapted to be selectively connected to pressure sensing conduits 136 and 138 which open into the respective flow areas $A_2$ and $A_1$. Motor operated valves 97 and 99 are interposed in the conduits 136 and 138 for selective measurement of the pressures in the flow area $A_1$ and the flow area $A_2$.

The following analysis takes into account the frictional presssure losses incurred in bringing the flowstream entering the chamber 128 through the conduit 122 to a halt and then accelerating the flowstream as it leaves the chamber 128 and flows to the conduit 132. The pressure measured in the conduit 138 indicating the static pressure in the passage defined by the cross sectional area $A_1$ will be designated $P_4$, the static pressure measured in the chamber 128 at the endwall 130 will be designated $P_5$ and the pressure measured in the conduit 136 indicating the static pressure in the flowpath having the cross sectional area $A_2$ will be designated $P_6$. If the frictional loss of pressure in stopping the flowstream is $U_1$ then:

$$P_5 - P_4 = \frac{m_t V_1}{g(A_1 + A_2)} - U_1 \quad (17)$$

Moreover, the pressure change between the endwall 130 and the conduit 132 which will be caused by acceleration of the flowstream will be $m_t V_2/g(A_1+A_2)$. In this case, the frictional pressure loss will add to the pressure change rather than subtract from it. Accordingly, $$P_5 - P_6 = \frac{m_t V_2}{g(A_1 + A_2)} + U_2 \quad (18)$$

if P is the density of both flow streams, then $V_2 = V_1(A_1/A_2)$. Making this substitution, the sum of the incoming and outgoing pressure changes is:

$$2P_5 - P_4 - P_6 = \frac{m_t V_1}{A_2 g} + U_2 - U_1 \quad (19)$$

Multiplying both sides of this equation (19) by $\rho A_1$ allows elimination of the quantity $V_1$ and the following equation may be derived:

$$m_t = \sqrt{A_1 A_2 \rho g} \cdot \sqrt{2P_5 - P_4 - P_6 + U_1 - U_2} \quad (20)$$

Of course, if it is assumed that the incoming frictional pressure loss $U_1$ equals the outgoing frictional pressure loss $U_2$, then these two quantities cancel each other and the equation for mass flow rate, $m_t$, can be solved by measuring pressures and density. A symmetrical flow path for both incoming and outgoing flow streams is necessary for this assumption to be valid.

Although preferred embodiments of the present invention have been described in detail herein, those skilled in the art will recognize that various substitutions and modifications may be made to the specific embodiments shown and described without departing from the scope and spirit of the invention as recited in the appended claims.

What is claimed is:

1. A system for determining the flow rate of a multiphase fluid flowstream comprising a gas and at least two liquids of different density comprising:
   conduit means including a conduit section for changing the direction of flow of said fluid flowstream;
   pressure differential measurement means interposed in said conduit means for measuring the change in pressure encountered by said fluid flowstream upon said change in direction;
   means for measuring the total density of said fluid flowstream;
   means for withdrawing a sample of said fluid flowstream and for separating the gas phase from the liquid mixture; and
   means for determining the fraction of one liquid in the other.

2. The system set forth in claim 1 wherein:
   said means for determining the fraction of one liquid in the other comprises a liquid conduit through which said liquid is conducted and microwave frequency range conductor means including a portion of said liquid conduit for determining the fraction of one liquid in the other by the change in microwave transmissivity through said conductor in the presence of said liquid mixture.

3. The system set forth in claim 1 wherein:
   the fraction of one liquid in the other is determined by comparing the difference in pressure between a column of liquid mixture separated from said flowstream and a column of liquid which is one of the two known liquids in said liquid mixture whereby the fraction of one of the liquids may be determined from said difference in pressure, the height of said columns and the difference in densities of the two liquids of said liquid mixture.

4. The system set forth in claim 1 including:
   means for measuring the density of said flowstream comprising portions of said conduit means which are at different vertical elevations, means for measuring the pressure differential between said portions of said conduit means at said different elevations whereby the density of said flowstream may be determined by dividing differential by the vertical distance the measured pressure between the points of measurement of the pressure differential.

5. The system set forth in claim 1 wherein:
   said conduit section for causing the change in direction of said fluid includes a conduit portion forming a nozzle interposed in said conduit section, a conduit disposed around said nozzle and having an effective cross-sectional flow area greater than said nozzle and providing a flow path which forces said flowstream to reverse its direction of flow upon emitting from said nozzle, and means for measuring he differential pressure between the point of reversal of flow and one of said nozzle or said conduit section downstream of said point of reversal of flow.

6. The system set forth in claim 1 wherein:
   said conduit section for causing the change in direction of said fluid includes a first conduit, a transverse endwall and a second conduit, said first and second conduits being in flow communication with said end wall, and said first and second conduits having substantially equal cross sectional flow areas and being substantially symmetrical whereby the frictional pressure losses from changing the direction of fluid flow will not affect measurement of the change in pressure encountered by said flowstream from said change of direction.

7. The system set forth in claim 1 wherein:
   said means for measuring the total density of said fluid flowstream comprises a gamma ray densitometer mounted for measuring the density of said fluid flowstream flowing through said conduit means.

8. The system set forth in claim 1 including:
   means for monitoring the temperature and pressure of said fluid flowstream for determining the densities of components of said fluid flowstream at the conditions under which the flow rate of said components is being measured.

9. The system set forth in claim 5 wherein:
   said conduit means includes a first conduit section having a portion which changes the elevation of said first conduit section from a first elevation to a second elevation, said conduit section including a nozzle, a further conduit section disposed around said nozzle and forming a flow path for reversing the direction of flow of said fluid flowstream, said further conduit portion having a portion forming a first elevation and a second elevation, and means for measuring the pressure in said respective conduit sections at said first elevations and said second elevations for determining the pressure difference at said first and second elevations whereby the density of said fluid flow stream may be determined.

10. A method for determining the mass flow rate of the components of a multiphase fluid flowstream comprising at least one gas and at least two liquids of different densities comprising the steps of:
    providing conduit means for conducting said fluid flowstream from a source of said fluid flowstream to a point of delivery, said conduit means including means forming a conduit section for substantially changing the direction of flow of said fluid flowstream, means for treating a sample of said fluid flowstream to separate the gas from the liquid mixture, means for determining the total density of said fluid flowstream and means for determining the respective fractions of said at least two liquids in said liquid mixture;

measuring the total density of said fluid flowstream;

conducting said fluid flowstream through said conduit section for changing the direction of flow and measuring the pressure differential encountered as a result of the change of direction of said fluid flowstream;

determining the flow area of said conduit section through which the flowstream is conducted to undergo the change of pressure as a result of the change of direction and determining the total mass flow rate of said fluid flowstream based on said change in pressure, said total density, and said flow area;

determining the density of said components of said fluid flowstream including said gas and said at least two liquids in said liquid mixture;

separating the liquids of said fluid flowstream from the gas to form a liquid mixture;

determining the fraction of one liquid in the liquid mixture;

determining the density of the liquid mixture ($\rho_L$) from the equation:

$$\rho_L = \rho_o(1-b) + \rho_w b$$

wherein $p_w$ is the density o said one liquid, $p_o$ is the density of the other of the liquids and b is the fraction of said one liquid in the liquid mixture;

determining the fraction of gas in said fluid flowstream based on the total density of the fluid flowstream, the density of the liquid mixture and the density of the gas; and determining the mass flowrate of the gas, and the respective ones of the at least two liquids in said liquid mixture using the densities of said components of said fluid flowstream, the total mass flowrate and the fractions of gas and said one liquid.

11. The method set forth in claim 10 wherein:
the step of measuring the total density of said fluid flowstream comprises passing said fluid flowstream through a conduit portion having a change in elevation, measuring the pressure differential in said conduit portion over said change in elevation and determining the density from the pressure differential and the change in height at the points of measuring said pressure differential.

12. The method set forth in claim 10 wherein:
the step of measuring total density is carried out using a densitometer interposed in said conduit means.

13. The method set forth in claim 10 wherein:
the step of determining the fraction of said one liquid in said liquid mixture comprises passing said liquid mixture through mans for measuring the change in microwave radiation transmissivity based on the fraction of said one fluid in the liquid mixture and comparing the change in transmissivity with known changes corresponding to known fractions of said one liquid in said liquid mixture.

14. The method set forth in claim 10 wherein:
the step of determining the fraction of said one liquid in said liquid mixture comprises comparing a column of said liquid mixture with a column of equal height containing one of the liquids of said liquid mixture and measuring the pressure difference between said columns.

15. The method set forth in claim 10 wherein:
the step of determining the fraction of gas in said fluid flowstream comprises:
comparing the total density of the fluid flowstream, the liquid density, and the gas density to determine the value (n) from the equation:

$$\rho_t = \rho_L(-n) + \rho_g n.$$

16. A method for determining the mass flow rate of the components of a multiphase fluid flowstream comprising at least one gas and two liquids of different densities comprising the steps of:

providing conduit means including means forming a conduit section for substantially reversing the direction of flow of said fluid flowstream, means for withdrawing a sample of said fluid flowstream to separate said gas from the liquid mixture, means for determining the total density of said fluid flowstream and means for determining the respective volumetric fractions of said two liquids in said liquid mixture;

measuring the total density of said fluid flowstream;

conducting said fluid flowstream through said conduit section for reversing said direction of flow and measuring a pressure differential encountered as a result of the change of directon of said fluid flowstream;

determining the flow area of said conduit section through which said fluid flowstream is conducted to undergo the change of pressure as a result of the reversal of direction flow and determining the total mass flow rate of said fluid flowstream based on said change of pressure, said total density, and said flow area;

determining the density of said components of said fluid flowstream including said gas and said two liquids in said liquid mixture;

withdrawing a sample of fluid from said fluid flowstream and separating said liquids from said gas to form a liquid mixture;

measuring the fraction of one liquid in the liquid mixture;

determining the density of the liquid mixture ($\rho_L$) from the equation:

$$\rho_L = \rho_o(1-b) + \rho_w b$$

wherein $p_w$ is the density of said one liquid, $\rho_o$ is the density of the other of the liquids and b is the fraction of said one liquid in the liquid mixture;

determining the fraction of gas in said from the equation:

$$\rho_t = \rho_L(1-n) + \rho_g n$$

wherein $\rho_g$ is the density of the gas and n is the fraction of gas in the fluid flowstream;

determining the mass flowrate of the gas, and the respective ones of the at least two liquids in said liquid mixture using the densities of said components of said fluid flowstream, the total mass flowrate and the fractions of gas and said one liquid.

17. The method set forth in claim 16 wherein:

the step of providing said conduit means includes providing a conduit section having a first conduit and a second conduit and a transverse endwall, said first and second conduits being of substantially equal cross sectional flow area and being substantially symmetrical whereby frictional pressure losses of said liquid mixture during flow reversal in said conduit section may be eliminated from said pressure differential measurement.

* * * * *

UNITED STATES PATENT AND TRADEMARK OFFICE
CERTIFICATE OF CORRECTION

PATENT NO. : 4,776,210

DATED : October 11, 1988

INVENTOR(S) : Lloyd A. Baillie, Frank H. Hsu, and Y. Sam Yang

It is certified that error appears in the above-identified patent and that said Letters Patent is hereby corrected as shown below:

Column 10, line 4 after "dividing" insert -- the measured pressure --, and continue with the next word "differential" as part of the same paragraph.

Column 10, lines 5 and 6 after "distance" delete the words "the measured pressure".

Column 10, line 17 delete "he" and insert -- the --.

Column 11, line 32 delete "o" and insert -- of --.

Column 11, line 59 delete "mans" and insert -- means --.

Column 12, line 11 (in the equation) delete "(-n)" and insert -- (1-n) --.

Signed and Sealed this

Sixth Day of June, 1989

*Attest:*

DONALD J. QUIGG

*Attesting Officer*  *Commissioner of Patents and Trademarks*